US00PP29393P2

(12) United States Plant Patent
Hansen

(10) Patent No.: US PP29,393 P2
(45) Date of Patent: Jun. 12, 2018

(54) **X *MANGAVE* PLANT NAMED 'MISSION TO MARS'**

(50) Latin Name: ×***Mangave* times *Agave***
Varietal Denomination: Mission to Mars

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days. days.

(21) Appl. No.: 15/530,444

(22) Filed: Jan. 13, 2017

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373, 372
CPC ..... A01H 5/12
See application file for complete search history.

*Primary Examiner* — Kent L Bell

(57) ABSTRACT

A new and unique ×*Mangave* plant named 'Mission to Mars' characterized by long, fleshy, horizontal to slightly arching, with typically overlapping, irregular, bright reddish-purple spotting covering large portions of leaves. Leaf margin has firm, medium-sized teeth. Growth rate is rapid to moderate.

1 Drawing Sheet

Botanical classification: hybrid; ×*Mangave* times *Agave*.
Variety denomination: 'Mission to Mars'.

BACKGROUND OF THE INVENTION

The present invention relates to the new and distinct ×*Mangave* hybrid plant, ×*Mangave* 'Mission to Mars' hybridized by the inventor at a wholesale perennial nursery in Zeeland, Mich., USA as cross between a proprietary unreleased hybrid known only by the breeder code ×*Mangave* PDN#9 (not patented) as the female or seed parent times an unnamed selection of *Agave shawii* (not patented) as the male or pollen parent. The cross was performed in the summer of 2012 and seeds were harvested and sown on Sep. 10, 2012. Through trials at the same nursery the plant was originally assigned the breeder code XMANG-12-80-05. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of ×*Mangave* 'Mission to Mars' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

×*Mangave* 'Mission to Mars' differs from its parents as well as all other *Manfreda, Agave* and ×*Mangave* known to the applicant. The most similar known cultivars are ×*Mangave* 'Moonglow' U.S. Plant patent application Ser. No. 15/330,178 and ×*Mangave* 'Lavender Lady' Co-pending U.S. Plant patent application Ser. No. 15/530,442. Compared with the female parent, the new plant has with greater coverage of a more reddish-purple color, leaves are more upright and less arched. Compared with the male parent the new plant has longer, thinner and more flexible foliage with greater coverage of bright reddish-purple coloration. 'Moonglow' differs from the new plant in having shorter, more narrow foliage that has less dense and darker or more greyed purple spotting. Compared with 'Lavender Lady' the new plant has longer and more gladiate leaves, fewer leaves per clump that are more flexible and the color of the leaves is brighter reddish-purple. Compared to 'Pineapple Express' U.S. Plant Pat. No. 28,613 the new plant has longer and broader leaves that have greater coverage of more bright reddish-purple coloration. Compared with 'Bloodspot' (not patented) the new plant has longer and broader foliage with the new plant also having with greater coverage of more bright reddish-purple coloration.

The new plant, 'Mission to Mars', is unique from all of the above cultivars and all *Agave,* ×*Mangave* and *Manfreda* known to the inventor by the following combined traits:

1. Long, fleshy, slightly folded, bright reddish-purple foliage in full sun and bluish-green with reddish-purple splotches when grown in less ultraviolet light, initially shiny and becoming glaucous;
2. Foliage develops large portions, especially toward center and base, of irregular, typically-overlapping bright reddish-purple spots throughout upper and lower surfaces;
3. Medium-sized, teeth on leaves firm and sharp;
4. Moderate to rapid growth rate.

BRIEF DESCRIPTION OF THE DRAWING

The photograph of ×*Mangave* 'Mission to Mars'; demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

The illustration shows the new plant having been grown in a container.

DETAILED BOTANICAL DESCRIPTION

The following descriptions and color references are based on the 2001 edition of The Royal Horticultural Society Colour Chart except where common dictionary terms are used. The new plant, ×*Mangave* 'Mission to Mars', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Parentage: ×*Mangave* PDN#9 (not patented) is a selected cross of *Manfreda jaliscana*×*Agave parryi* 'J.C. Raulston' as the female or seed parent; an unnamed selection of *Agave shawii* (not patented) as the male or pollen parent;

Propagation: Division of side shoots and sterile shoot-tip tissue culture;

Time to initiate roots from tissue culture: About 21 days;

Growth rate: Moderate to rapid;

Crop time: About 12 to 14 weeks to finish in a 3.8 liter container from a 35 mm tissue culture growing at about 21° C.;

Rooting habit: Fleshy, lightly branching, with roots up to 15 cm long;

Root color: Nearest RHS 158C;

Plant shape and habit: Succulent herbaceous perennial with basal rosettes of about 30 leaves radially emerging and slightly arching from central rhizome extending slightly below the base of the plant when grown in containers, producing a radially-symmetrical, rounded mound;

Plant size: Foliage height about 25.0 cm tall from soil line to the top of the leaves and about 56.0 cm wide at the widest point slightly below soil line in container;

Foliage description: Gladiate; simple; margins coarsely dentate; apex narrowly acute; base truncate, sessile, clasping; slightly concaved; bi-laterally symmetrical; with large portions covered with overlapping reddish-purple spots; glaucous both surfaces with young leaves lustrous adaxial;

Leaf size: To about 40.0 cm long, about 6.8 cm wide at base and about 4.0 mm thick; average about 38.0 cm long, about 6.0 cm wide and about 4.0 mm thick;

Foliage fragrance: None observed;

Leaf blade color:

*Adaxial* (*mature*).—Blend of between RHS 138A and lighter than RHS 134A with spots to nearly solid portions especially toward center and base of leaves of between RHS 187A and RHS 187B; greyed dark reddish spots becoming more pronounced with greater ultraviolet light exposure.

*Abaxial* (*mature*).—Blend between RHS 138A and RHS 138B with large, frequently-overlapping spots about 10.0 to 12.0 mm across of between RHS 187B and RHS 187A.

*Adaxial* (*young*).—Nearest RHS 137A blotched with nearest RHS 138A.

*Abaxial* (*young*).—Nearest RHS 137A and blotched with nearest RHS 138A.

*Teeth*.—Sharp; about 2.0 mm long and between six and twelve per 2.5 cm of margin, more concentrated proximally; color (young) nearest RHS 164B; (mature) nearest RHS 187A.

Spine: Becoming dry and firm, emarginate; about 1.4 cm long and 2.0 mm diameter at base; color on young leaves blend between RHS N170A and RHS 166B, at maturity blend between RHS 177A and RHS 178A;

Petiole: Sessile;

Veins: Parallel; not distinct abaxial or adaxial;

Flower description: Not yet observed;

Fruit and seed: Not yet observed;

Disease resistance: ×*Mangave* 'Mission to Mars' has not been observed to be resistant to diseases beyond that which is normal for ×*Mangave, Agave* or *Manfreda*. The plant is xeromorphic and survives well with minimal water once established. The new plant is hardy at least from USDA zone 8b to 10. Full extent of winter hardiness has not been tested.

It is claimed:

1. A new and distinct cultivar of ornamental ×*Mangave* plant named 'Mission to Mars' as herein described and illustrated, suitable for the garden or as a potted plant in the garden or home.

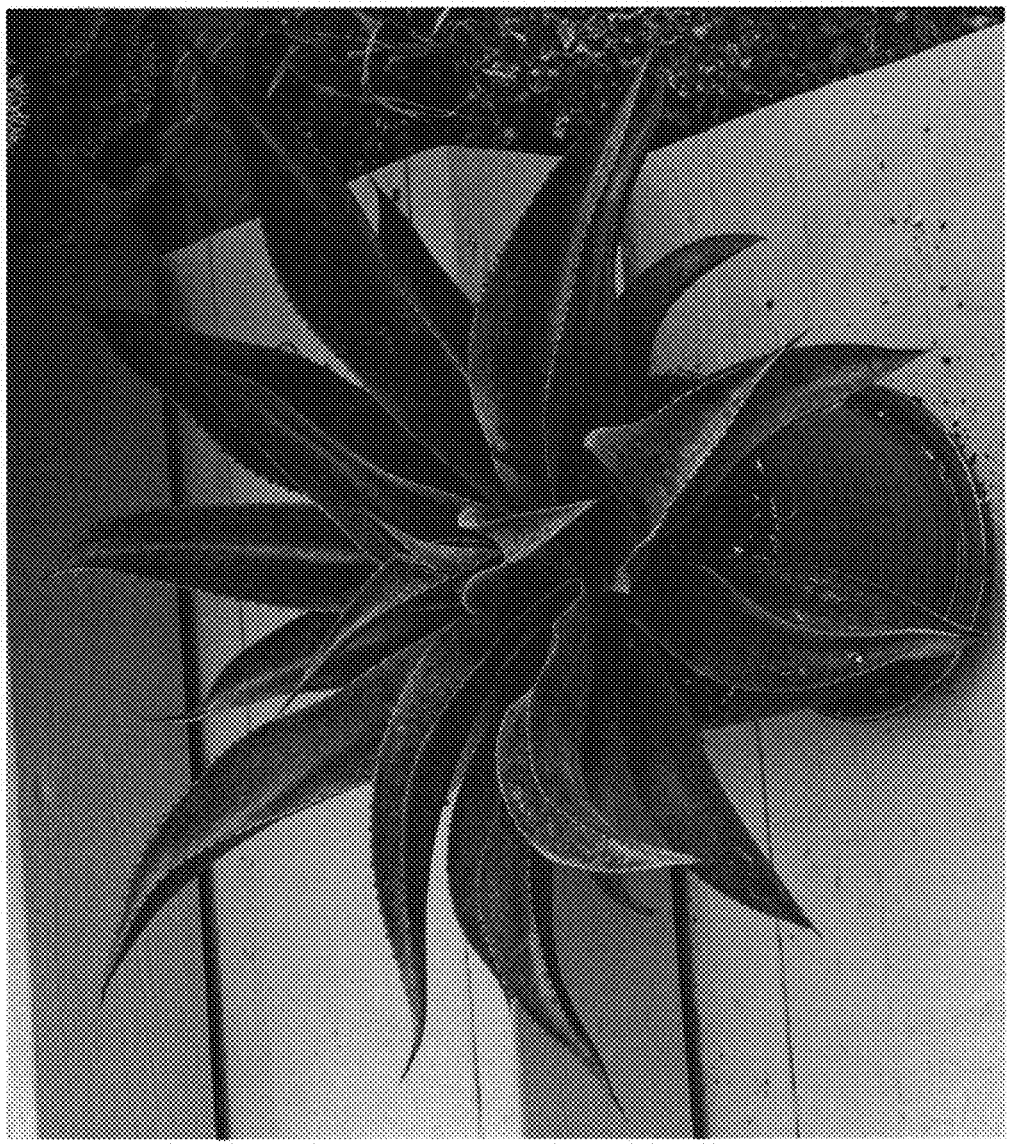

* * * * *